United States Patent

Selden et al.

(10) Patent No.: US 9,402,944 B2
(45) Date of Patent: Aug. 2, 2016

(54) MULTI-FUNCTIONAL CHAMBER FOR HOUSING A BIOLOGICAL COMPONENT

(75) Inventors: Clare Selden, London (GB); Humphrey Hodgson, London (GB); Sam Coward, Suffolk (GB)

(73) Assignee: University College London (GB)

( * ) Notice: Subject to any disclaimer, the term of this patent is extended or adjusted under 35 U.S.C. 154(b) by 1398 days.

(21) Appl. No.: 12/667,323

(22) PCT Filed: Jun. 25, 2008

(86) PCT No.: PCT/GB2008/002227
§ 371 (c)(1),
(2), (4) Date: Jan. 31, 2011

(87) PCT Pub. No.: WO2009/007678
PCT Pub. Date: Jan. 15, 2009

(65) Prior Publication Data
US 2011/0125286 A1 May 26, 2011

(30) Foreign Application Priority Data

Jul. 6, 2007 (GB) .................................. 0713595.7

(51) Int. Cl.
*C12M 3/02* (2006.01)
*A61M 1/34* (2006.01)
(Continued)

(52) U.S. Cl.
CPC ............... *A61M 1/3472* (2013.01); *A01N 1/02* (2013.01); *A01N 1/0247* (2013.01); *A61M 1/3489* (2014.02); *A61M 1/3689* (2014.02); *C12M 21/08* (2013.01); *C12M 23/06* (2013.01); *C12M 25/16* (2013.01); *C12M 29/04* (2013.01); *C12M 41/24* (2013.01); *C12N 5/0671* (2013.01);
(Continued)

(58) Field of Classification Search
CPC ...... C12M 21/08; C12M 23/34; C12M 29/04; C12M 41/24; A61M 1/3489
USPC .............................................. 435/299.1, 297.2
See application file for complete search history.

(56) References Cited

U.S. PATENT DOCUMENTS 3,963,581 A * 6/1976 Giacobbe et al. .......... 435/295.2
4,311,589 A 1/1982 Brumfield
(Continued)

FOREIGN PATENT DOCUMENTS

DE 102004053164 A1 5/2006
EP 0 950 932 A1 10/1999
(Continued)

OTHER PUBLICATIONS

Combined Search and Examination Report dated Oct. 17, 2007.
(Continued)

*Primary Examiner* — William H Beisner
(74) *Attorney, Agent, or Firm* — Fishman Stewart PLLC

(57) ABSTRACT

The present invention relates to the field of extracorporeal liver perfusion and, more particularly, to the design of a chamber in which a biological component can be housed to form e.g. a bio-artificial liver (BAL). It also relates to a bio-artificial liver per se, it's components and methodological steps associated with its development and use. The chamber (10) for the biological component (100) of a bio-artificial liver (200) is configured to allow: • Proliferation of the biological component, in situ; • Cryopreservation of the biological component, in situ, and • Perfusion of the biological component, in situ.

16 Claims, 4 Drawing Sheets

(51) Int. Cl.

| | |
|---|---|
| *A01N 1/02* | (2006.01) |
| *C12M 3/00* | (2006.01) |
| *C12M 1/12* | (2006.01) |
| *C12M 1/00* | (2006.01) |
| *C12M 1/02* | (2006.01) |
| *C12N 5/071* | (2010.01) |
| *A61M 1/36* | (2006.01) |
| *A61F 2/02* | (2006.01) |

(52) U.S. Cl.
CPC ............ *A61F 2/022* (2013.01); *C12N 2511/00* (2013.01); *C12N 2533/74* (2013.01)

(56) References Cited

U.S. PATENT DOCUMENTS

| | | | |
|---|---|---|---|
| 4,649,114 A * | 3/1987 | Miltenburger et al. | 435/401 |
| 4,778,653 A * | 10/1988 | Kamimura et al. | 422/6 |
| 5,270,192 A * | 12/1993 | Li | A61M 1/3472 435/174 |
| 5,707,868 A * | 1/1998 | Boulay et al. | 435/383 |
| 5,885,826 A | 3/1999 | Worden et al. | |
| 6,174,719 B1 | 1/2001 | Elizondo et al. | |
| 6,218,182 B1 * | 4/2001 | Naughton et al. | 435/395 |
| 2002/0168758 A1 | 11/2002 | Martinez et al. | |
| 2004/0033593 A1 * | 2/2004 | Hochleitner et al. | 435/295.3 |
| 2005/0180878 A1 | 8/2005 | Messier | |

FOREIGN PATENT DOCUMENTS

| | | |
|---|---|---|
| WO | WO-93/16171 A1 | 8/1993 |
| WO | WO-96/09876 A1 | 4/1996 |
| WO | WO-00/78932 A1 | 12/2000 |

OTHER PUBLICATIONS

International Search Report dated Mar. 16, 2009.
English abstract for EP-0 950 932-A1.
Inn-Kyu, K. et al., "Morphology and metabolism of Ba-alginate encapsulated hepatocytes with galactosylated poly (ally amine) and poly (vinyl alcohol) as extracellular matrices", Journal of Materials Science, Materials in Medicine, vol. 16, No. 6, Jun. 2005, 533-539.
Matthew, H. W. et al., "Performance of a Plasma-Perfused, Microencapsulated Hepatocytes: Prospects for Extracorporeal Liver Support", Journal of Pediatric Surgery, vol. 28, No. 11, Nov. 1993, 1423.
Khalil, M. et al., "Human hepatocyte cell lines proliferating as cohesive spheroid colonies in alginate markedly upregulate both synthetic and detoxificatory liver function", Journal of Hepatology, Jan. 2001, 68-77.
Bertrand, David et al., In Vitro Assessment of Encapsulated C3A Hepatocytes Functions in a Fluidized Bed Bioreactor, Biotechnology Progress, vol. 20, No. 4, Jul. 2004, 1204-1212.
Kinasiewicz, A. et al., "Three-Dimensional growth of human hepatoma C3A cells within alginate beads for fluidized bioartificial liver", The International Journal of Artificial Organs, vol. 31, No. 4, Apr. 2008, 340-347.
Coward, S. M. et al., "Alginate-encapsulated HepG2 Cells in a Fluidized Bed Bioreactor Maintain Function in Human Liver Failure Plasma", Artificial Organs, vol. 33, No. 12, 2009, 1117-1126.
Kinasiewicz, A. et al., "Culture of C3A Cells in Alginate Beads for Fluidized Bed Bioartificial Liver", Transplantation Proceedings, Orlando, FL, US, vol. 39, No. 9, Nov. 20, 2007, 2911-2913.
Chung, Y. et al., "Human Embryonic Stem Cell Lines Generated without Embryo Destruction", Cell Stem Cell, Elsevier, Cell Press, Amsterdam, vol. 2, No. 2, Feb. 7, 2008, 113-117.
Chan, C. et al., "Application of Multivariate Analysis to Optimize Function of Cultured Hepatocytes", Biotechnology Progress, American Institute of Chemical Engineers, US, vol. 19, No. 2, Mar. 1, 2003, 580-598.
Fiegel, H. C. et al., "Hepatic tissue engineering: from transplantation to customized cell-based liver directed therapies from the laboratory", Journal of Cellular and Molecular Medicine, vol. 12, No. 1, Jan. 2008, 56-66.
Vorlop et al, Design of calciumalginate immobilized yeast cell beads with controlled low density to enhance their fludization behavioiur in bioreactors; Biotechnology Technniques 7 (1993); p. 287-292.
Sun et al, Improving mechanical stability and density distribution of hepatocyte microcapsules by fibrin clot and gold nano-particles; Journal of Biotechnology 111 (2007); p. 169-177.
Legallais et al., "Design of fluidized bed bioartificial liver", Artificial Organs 24 (2000); ; pp. 519-525.
Schwinger et al., "High throughput encapsulation of murine fibroblasts in alginate using the jetcutter technology", Journal of Microencapsulation 19 (2002); pp. 273-280.
Koch et al., "Alginate encapsulation of genetically engineered mammalian cells: Comparison of production devices, methods and microcapsule characteristices", Journal of Microencapsulation 20 (2003); pp. 303-316.
Coward et al., "Proliferation rates of HepG2 cells encapsulated in a microgravity environment compared with static cultures", Artificial Organs 29 (2004); pp. 152-158.
Coward et al., Alginate-encapsulated HepG2 cells in a pilot-scale fluidised bed bioreactor maintain performance in human liver failure plasma makiing them suitable for use in a bioartificial liver; Journal of Hepatology 44; pp. S53-S54, abstract 118, (Sep. 6, 2010).
Search Report for GB1001916.4, (Jun. 7, 2010).
Search Report for EP08762515.8, (Jun. 30, 2010).
US 6,465,252, 10/2002, Toner et al. (withdrawn)

* cited by examiner 100    110    120

100    110    120    130

MULTI-FUNCTIONAL CHAMBER FOR HOUSING A BIOLOGICAL COMPONENT

CROSS-REFERENCES TO RELATED APPLICATION

This application claims priority to International Patent Application PCT/GB2008/002227, which claims priority to European application GB 0713595.7, filed Jul. 6, 20007, each of which are hereby incorporated by reference in their entirety.

TECHNICAL FIELD

The present invention relates to the field of extracorporeal liver perfusion and, more particularly, to the design of a chamber in which a biological component can be housed to form e.g. a bio-artificial liver (BAL). It also relates to a bio-artificial liver per se, it's components and methodological steps associated with its development and use.

BACKGROUND OF THE INVENTION

Currently, the sole cure for both acute and chronic liver disease and liver failure is transplantation. However, this treatment is restricted by a lack of donor organs. In the US alone, 17,000 patients are on the transplant waiting list. Many of them die whilst waiting for a transplant. There is therefore an urgent need for a device which can temporarily perform the function of a patient's liver, keeping them alive whilst a suitable donor organ is found, or which provides an environment which ensures the patient does not die whilst the patient's own liver recovers sufficient functionality for the patient's survival.

There are two principal types of liver machines:
A purely artificial machine; and
A bio-artificial machine.

Both rely on perfusion of a patient's plasma or blood into an extracorporeal circuit for a period of 6 h or more.

Purely artificial systems exist and a number of bio-artificial systems are in development.

Purely artificial systems, such as albumin dialysis, are however unable to replace all the liver functions including:
Detoxification,
Biotransformation,
Synthesis, and
Storage and whilst they have proved relatively safe in clinical trials they have not given rise to a significant improvement in patient survival.

The purely artificial systems are solely physical/chemical in nature, and provide a detoxification function by adsorption/exchange on e.g. resin, charcoal, ion exchange columns or albumin, or combinations of these.

In contrast the bio-artificial livers (BALs) contain a biological component, i.e. liver cells, either alone, or in conjunction with an artificial device as a hybrid system. The hypothesis underlying the incorporation of liver cells is that liver function is so complex, comprising multiple synthetic, detoxification, and metabolic pathways, that crude mechanical devices will always be inadequate to replace the range of function desired; furthermore the functions critical to buying time for liver function to recover, have not been fully defined and the use of liver cells allows both defined and undefined functions to be replaced. For the biological component, isolated liver cells or occasionally liver slices are used, and systems have used either human or animal (most often porcine) cells.

The majority of early BALs used hollow fibre cartridges in which cells were separated from plasma or whole blood by a membrane. Pore sizes of the membrane differed between systems, some limited to transfer of molecules <10,000 daltons, some with pore sizes as large as 2 micron.

More recently other configurations have emerged which better address mass transfer limitations. They include:

An AMC-BAL which contains cells attached to a polyester matrix which is exposed directly to oxygenated plasma, (Flendrig L M, LaSoe J W, Jorning G G A, Steenbeek A, Karlsen O T, Bovee W M M J, Ladiges N C J J, TeVelde A A, Chamuleau R A F M. In vitro evaluation of a novel bioreactor based on an integral oxygenator and a spirally wound non-woven polyester matrix for hepatocyte culture as small aggregates. Journal of Hepatology 1998; 26: 1379-1392.)

A non-woven fabric bioreactor, (Li L J, Du W B, Zhang Y M, Li J, Pan X P, Chen J J, Cao H C, Chen Y, Chen Y M. Evaluation of a bioartificial liver based on a non-woven fabric bioreactor with porcine hepatocytes in pigs. Journal of Hepatology 2006; 44: 317-324.)

A radial flow bioreactor, (Morsiani E, Brogli M, Galavotti D, Bellini T, Ricci D, Pazzi P, Puviani A C. Long-term expression of highly differentiated functions by isolated porcine hepatocytes perfused in a radial-flow bioreactor. Artif. Organs 2001; 25: 740-748.) and The Innsbruck Bioartificial Liver containing hepatocyte aggregates. (Hochleitner B, Hengster P, Duo L, Bucher H, Klima G, Margreiter R. A novel bio-artificial liver with culture of porcine hepatocyte aggregates under simulated microgravity. Artif. Organs 2005; 29: 58-66.)

The above examples all use animal hepatocytes.

Examples of reactors with human cells include those using:

Primary hepatocytes, (Gerlach J C, Mutig K, Sauer I M, Schrade P, Efimova E, Mieder T, Naumann G, Grunwald A, Pless G, Mas A, Bachmann S, Neuhaus P, Zeilinger K. Use of primary human liver cells originating from discarded grafts in a bioreactor for liver support therapy and the prospects of culturing adult liver stem cells in bioreactors: a morphologic study. Transplantation 2003; 76: 781-786.)

Hollow fibre cartridges using well-differentiated tumour-derived cell lines such as C3A cells, (Ellis A J, Hughes R D, Wendon J A, Dunne J, Langley P G, Kelly J H, Gislason G T, Sussman N L, Williams R. Pilot-controlled trial of the extracorporeal liver assist device in acute liver failure. Hepatology 1996; 24: 1446-1451.) and A fluidised bed bioreactor with human C3A cells encapsulated at high (about 1 million cells/ml) density into alginate. (David B, Dufresne M, Nagel M D, Legallais C. In vitro assessment of encapsulated C3A hepatocytes functions in a fluidized bed bioreactor. Biotechnol. Prog. 2004; 20: 1204-1212.)

Various groups around the world are working with different biological components including:
The use of primary cultures of human hepatocytes;
The use of primary cultures of pig hepatocytes; and
The use of C3A cells—a proliferating cell line initially derived from a well developed human liver cell tumour.

There are fundamental differences between any system which uses proliferating cell lines and those which use primary cells. Proliferating cell lines can be seeded singly and multiply, in situ, to form cohesive spheroids over a period of time, dependent on the doubling time of a specific cell type. In contrast, primary cells even if seeded at a very high cell density will not necessarily form close cell to cell contacts and therefore will not necessarily give rise to a true 3-dimensional environment, which is associated with up-regulation of function, as it mimics the in vivo situation.

The applicant's approach has been to use a cell line, and has similarities with the C3A approach which has not proved effective in clinical trials. However, the applicant's cell line is different and has some different functional properties. There are also fundamental differences between the housing and initial culture of the cells prior to use.

Previously, C3A cells have been used either in:
"Hollow fibre cartridge culture configuration", or
"Uncultured", in a fluidised bed in low occupancy alginate beads.

This is in contrast to the methodology used by the applicant, who uses an uncoated alginate matrix in a fluidised bed bioreactor configuration with pre-culture of encapsulated cells to performance competence.

The applicant's biological component, which comprises human hepatocyte cell lines cultured in a 3-D configuration, has been demonstrated, at lab scale, to provide functional liver capacity on a per cell basis, which approaches that seen in vivo for several of the liver's key functions including:
Clotting factor synthesis;
Steroid metabolism; and
Specified detoxification functions.

Fuller details on the expression of hepatocyte-specific function, pioneered by the applicant, are given below:

Applicant has pioneered (on a laboratory scale) the culture of human hepatocyte-derived cell lines as 3-dimensional (3-D) spheroid colonies in alginate beads, as disclosed in:
Selden C, Shariat A, McCloskey P, Ryder T, Roberts E, Hodgson H.
Three-dimensional in vitro cell culture leads to a marked upregulation of cell function in human hepatocyte cell lines—an important tool for the development of a bioartificial liver machine. Annals Of The New York Academy Of Science 1999; 875: 353-363;
McCloskey P, Edwards R J, Tootle R, Selden C, Roberts E, Hodgson H J. Resistance of three immortalized human hepatocyte cell lines to acetaminophen and N-acetyl-p-benzoquinoneimine toxicity. J Hepatol 1999; 31: 841-851;
Selden C, Khalil M, Hodgson H. Three dimensional culture upregulates extracellular matrix protein expression in human liver cell lines-a step towards mimicking the liver in vivo? Int J Artif Organs 2000; 23: 774-781;
Khalil M, Shariat-Panahi A, Tootle R, Ryder T, McCloskey P, Roberts E, Hodgson H, Selden C. Human hepatocyte cell lines proliferating as cohesive spheroid colonies in alginate markedly upregulate both synthetic and detoxificatory liver function. Journal Of Hepatology 2001; 34: 68-77;
McCloskey P, Tootle R, Selden C, Larsen F, Roberts E, Hodgson H J. Modulation of hepatocyte function in an immortalized human hepatocyte cell line following exposure to liver-failure plasma. Artif. Organs 2002; 26: 340-348; and
Coward S M, Selden C, Mantalaris A, Hodgson H J. Proliferation rates of HepG2 cells encapsulated in alginate are increased in a microgravity environment compared with static cultures. Artif. Organs 2005; 29: 152-158.

Each of these documents are incorporated by reference.

The advantages of this system are:
Cells proliferating in this milieu maintain a near-cuboidal cell architecture;
They have close cell-to-cell and cell-matrix organisation; and
They secrete extracellular matrix proteins and a large repertoire of liver specific secreted proteins as exemplified by:
Albumin,
Prothrombin,
Fibrinogen,
Alpha-1-antitrypsin, and
Alpha-1-acid glycoprotein.

They express many functions at levels equivalent to those of hepatocytes in vivo, e.g. steroid metabolism, glycogen synthesis etc.

The applicant has also shown that some functions are poorly expressed or missing, but can be supplemented. For example they have demonstrated that although HepG2 clones, including the C3A subclone which is the basis of one bio-artificial device, produce urea, this is via a urea-cycle independent mechanism that does not detoxify ammonia. Thus, unmodified, such cells are unlikely to be beneficial in treating the ammonia-dependent encephalopathy of liver failure. Using gene transfer to replace two missing enzymes they have demonstrated restoration of urea production from ammonia in their HepG2 clones. (Mavri-Damelin D, Eaton S, Damelin L H, Rees M, Hodgson H J, Selden C. Ornithine transcarbamylase and arginase I deficiency are responsible for diminished urea cycle function in the human hepatoblastoma cell line HepG2. Int. J Biochem. Cell Biol. 2006.

They have also characterised them extensively with respect to liver specific function as disclosed in:
(Khalil M, Shariat-Panahi A, Tootle R, Ryder T, McCloskey P, Roberts E, Hodgson H, Selden C. Human hepatocyte cell lines proliferating as cohesive spheroid colonies in alginate markedly up-regulate both synthetic and detoxificatory liver function. Journal Of Hepatology 2001; 34: 68-77;
Selden C, Shariat A, McCloskey P, Ryder T, Roberts E, Hodgson H. Three-dimensional in vitro cell culture leads to a marked upregulation of cell function in human hepatocyte cell lines—an important tool for the development of a bioartificial liver machine. Annals Of The New York Academy Of Science 1999; 875: 353-363; and
Selden C, Khalil M, Hodgson H. Three dimensional culture upregulates extracellular matrix protein expression in human liver cell lines—a step towards mimicking the liver in vivo? Int J Artif Organs 2000; 23: 774-781)
(All referred to previously) and
L H Damelin, M Kirwan, S Coward, P Collins, I J Cox, C Selden, H J F Hodgson. Fat-loaded insulin resistant HepG2 cells are resistant to cytokine and pro-oxidant induced damage, but become damage susceptible after down-regulation of AMP-activated kinase. BASL 2005; and
Selden C, Roberts E, Stamp G, Parker K, Winlove P, Ryder T, Platt H, Hodgson H. Comparison of three solid phase supports for promoting three-dimensional growth and function of human liver cell lines. Artif. Organs 1998; 22: 308-319.

(Also, incorporated by reference hereto) Additionally, in an animal model of fulminant liver failure, they have shown them to exhibit an improvement in clinical and biochemical parameters.

Rahman T M, Selden C, Khalil M, Diakanov I, Hodgson H J. Alginate-encapsulated human hepatoblastoma cells in an extracorporeal perfusion system improve some systemic parameters of liver failure in a xenogeneic model. Artif. Organs 2004; 28: 476-482; and Rahman T M, Selden A C, Hodgson H J. A novel model of acetaminophen-induced acute hepatic failure in rabbits. J Surg. Res. 2002; 106: 264-272.

(Also, incorporated by reference hereto)

Furthermore, they have demonstrated improved per bead performance by culture in a rotating cell culture system (RCCS) under simulated microgravity conditions:

Coward S M, Selden C, Mantalaris A, Hodgson H J. Proliferation rates of HepG2 cells encapsulated in alginate are increased in a microgravity environment compared with static cultures. Artif. Organs 2005; 29: 152-158 (Referred to previously); and Human liver cells in a pilot scale fluidised bed bioreactor maintain performance in human liver failure plasma, making them suitable for a bioartificial liver. Presented at World Congress of Biomechanics, Jul. 29-Aug. 4 2006 in Munich, Germany.

They have also tested the performance of this system in normal human plasma and plasma collected from patients with acute liver failure establishing that there is maintained viability and functional performance over 8 hours.

S. M. Coward, C. Legallais, M. Thomas, F. Tofteng, F. Larsen, H. J. Hodgson, C. Selden. Alginate-encapsulated Hepg2 cells in a pilot-scale fluidised bed bioreactor maintain performance in human liver failure plasma making them suitable for use in a bioartificial liver. Journal of Hepatology 44 [Suppl 2], S53. 2006.

(Also, incorporated by reference hereto)

However, the scale up of the biological component, from a laboratory scale size, involving no more than a 70 ml volume of alginate beads, provides significant challenges, some of which are addressed herein, the solutions to which may form the basis of independent claims.

Thus, for example, the biological component of the extracorporeal system should be:

Prepared to appropriate good manufacturing practice (GMP),

Readily transportable to centres where the patients will be hospitalised,

Conveniently packaged for storage, transport and charging a perfusion system;

Movable from the "cell-factory" through to the "clinic", for use in extracorporeal circulation.

U.S. Pat. No. 6,218,182 teaches a tissue engineering bioreactor for growing three dimensional tissue in which cells are seeded onto a mesh. After the tissue has been grown in the bioreactor, it is suggested that it can be frozen and preserved in the bioreactor container itself.

An aim of the present invention was to develop a chamber, sized for human use, into which the applicant could incorporate their, or another, biological component to form a bio-artificial liver that could benefit patients, but which may additionally be used to mimic a liver in drug metabolism and liver toxicity studies. In the latter case there would not necessarily be a need to cryo-preserve the cells.

This object is achieved by having a chamber, in which a biological component can be housed to form, for example, a bio-artificial liver (BAL), which is functionally modular in that it can retain the biological component in a manner which allows it to:

Proliferate the biological component (in situ);
Cryopreserve (both freeze and defrost) the biological component (in situ); and
Be perfused.

SUMMARY

According to a first aspect of the present invention there is provided a chamber for the biological component of a bio-artificial liver comprising a fluid bed support, a fluidising inlet and a fluidising outlet characterised in that is configured to allow:

Proliferation of the biological component, in situ;
Cryopreservation of the biological component, in situ, and
Perfusion of the biological component, in situ.

Preferably, the chamber is also designed such that it can be sterilised before the biological component is introduced into the chamber.

Preferably, the biological component comprises:

A cell line, most preferably Hep G2 cells;
A matrix forming agent, most preferably alginate beads; and
A density controlling agent, most preferably glass beads.

The cell line is encapsulated in the matrix forming agent together with the density controlling agent.

The encapsulation serves a number of functions:

It protects cells during freeze/thawing
It facilitates easy handling of the biomass
It allows for perfusion in a chamber or fluidised bed reactor; and
It provides a matrix allowing the cells to form a three dimensional mass.

That such alginate encapsulated cells may be suitable for scale up has been disclosed by the applicant—Coward et al Poster abstract Dec. 4-5 2006 (incorporated by reference).

The chamber serves as a fluidised bed reactor and comprises:

An inlet and outlet allowing for fluid flow across the chamber; and
A fluid bed support above which the encapsulated cells can be suspended.

The general concept of using a fluidised bed for perfusion has also been previously disclosed—Legallais et al, Artificial Organs 24(7):519-525. (Incorporated by reference.) It has not, however, been previously suggested that a fluidised bed could beneficially be used in the proliferation stage nor with cell spheroids, only with encapsulated single cell suspensions.

The fluid bed support preferably comprises a plate which is provided with a plurality of spaced holes, of not greater than 200 μm, which allow for controlled fluidisation of the bed. The bed has a filter overlaying it which is held in place by e.g. a wire ring. The plate is sealed within the chamber by, for example, an O-ring.

The chamber is preferably cylindrical and has an aspect ratio (a)=height (h)/diameter (d) of from 10:1 to 1.3:1. This is significant for two reasons: In its upright (vertical) position such an aspect ratio provides an optimum environment (mass/volume relationship characteristics) for initial cell proliferation and for use, i.e. for transfer of oxygen and nutrients to the cells and for transfer of proteins from the cells to e.g. plasma or culture medium. It also facilitates medium exchange prior to cryopreservation. (Rapid freezing/defrosting of cells.) In its horizontal position, (particularly when the aspect ratio approaches 10:1) the biological component can be "spread", such that a larger surface area thereof can be brought into contact with the outer wall of the chamber and heat exchange elements, thus facilitating better heating/cooling (with minimal disruption to fluidisation) due to the laterally displaced position of the heat exchange elements relative to the main chamber volume.

To further address the problem of getting sufficient oxygen to the cells, in a device scaled for human use (typically one of a size of from 1-10 liters volume capable of holding 0.5-5 l of a biological component and which should be capable of allowing for up to a two-fold expansion of volume on fluidisation) the chamber additionally comprised a fluid transport system disposed therein. The fluid transport system has a primary function of transporting gas to the biological component, but may additionally have a secondary function of transporting a heating or cooling fluid. In order to facilitate its primary function it is made of a gas permeable material and is disposed within the chamber in a manner that ensures a detrimental oxygen gradient does not build up, in use, from the inlet to outlet.

In one favoured embodiment the fluid transport system is disposed helically around the inner circumferential walls of the chamber.

In a further preferred embodiment the fluid transport system has a degree of compressibility, such that it can function as a "shock absorber" during cryo-preservation, thereby additionally providing a degree of protection to the encapsulated biological component.

According to a second aspect of the present invention there is provided a bioartificial liver device comprising a chamber of the invention filled with a biological component.

Furthermore the bioartificial liver device may comprise a solution, e.g. culture media (during proliferation), cryopreservant (during storage) or plasma (during perfusion).

According to a third aspect of the present invention there is provided a method of perfusing blood or plasma comprising introducing plasma or blood to a bioartificial liver device of the invention such that it enters the chamber via inlet and exits via outlet.

According to a fourth aspect of the present invention there is provided a scalable method for the manufacture of a biological component comprising a matrix forming agent containing a plurality of cells and one or more density modifiers comprising:
i. Preparing the matrix forming agent;
ii. Seeding the matrix forming agent with a plurality of cells;
iii. Densifying the matrix forming agent with a density modifier such that beads of the biological component will achieve continued suspension when perfused in human plasma;
iv. Passing the biological component through a shaped nozzle to form a stream,
v. Cutting the stream into beads; and
vi. Polymerising the beads.

Preferably the matrix forming agent is an alginate and it is seeded with $0.5 \times 10^6$ to $3.0 \times 10^6$ cells per ml of alginate, the density modifier is glass particles, the shaped nozzle is circular in cross section and has a diameter of 250-450 µm and the stream is cut with wire discs at a speed of from 3000 to 4000 rpm.

According to a fifth aspect of the present invention there is provided a scalable method for proliferating cells seeded in a matrix forming agent comprising:
1. Placing the cells seeded in the matrix forming agent in a chamber having a fluidised bed, and
2. Growing them to performance competence.

According to a sixth aspect of the present invention there is provided a method for cryopreserving proliferated cells in a chamber comprising a fluidised bed and one or a plurality of heat exchange elements disposed therein:

1. Exchanging cryoprotectant with the proliferated cells in the chamber;
2. Laying the chamber horizontal to allow distribution of the proliferated cells along a length (h) of the chamber; and
3. Rapidly cooling the proliferated cells by passing a coolant through the heat exchange elements.

According to a seventh aspect of the present invention there is provided a scaled bioartificial liver for use in drug metabolism and/or liver toxicity studies comprising a scalable chamber of the invention filled with a biological component.

BRIEF DESCRIPTION OF THE DRAWINGS

The various aspects of the invention are further described, by way of example only, with reference to the following figures in which.

DETAILED DESCRIPTION

Figure 1:
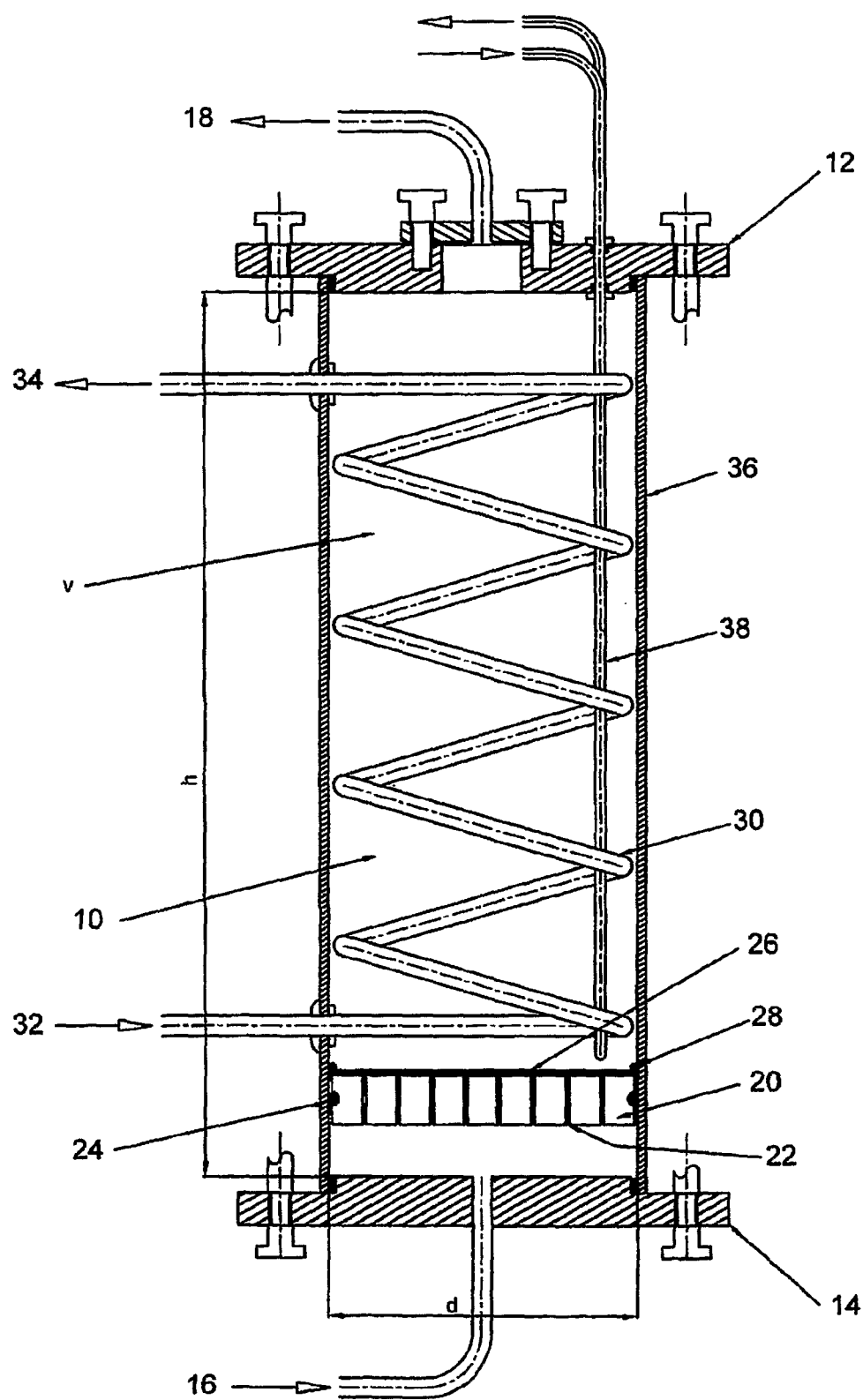
FIG. 1 is a cross sectional view of one embodiment of a chamber according to the invention.

The invention provides a "functionally modular" chamber in which epithelial cells, e.g. liver cells, can be housed and manipulated through various "development/life cycle" stages. Thus, for example, liver cells can serially be:
Cultured to performance competence;
Cryopreserved; and
Utilized in the same chamber, by for example, changing "solutions" and altering "conditions".

Thus, for example, a biological component, such as, alginate beads containing liver cells, may be prepared and delivered into the "functionally modular" chamber in which:
Initial proliferation to optimal cell mass and performance take place;
Subsequent cryopreservation can occur, and following transportation to a sick patient, and after thawing,
the cells can be perfused, in-line, in the same chamber in an extracorporeal circuit attached to the patient.

Thus, whilst the chamber (section 1.0) is central to the invention a biological component (section 2.0) is also required to form a bio-artificial liver device, (section 3.0) which can be used to perfuse a patient (section 4.0).

In order for the system to be realised it was independently necessary to develop scalable methods to:
Manufacture the biological component (section 5.0),
Proliferate the cells (section 6.0), and
Cryopreserve them (section 7.0).

Each of these aspects is described in detail below:
Additionally, and on a smaller scale, the development of alginate-encapsulated human liver cells expressing a high level of hepatocyte-specific drug-metabolising enzymes, optionally prepared in a cryopreserved transportable form, offers a valuable tool in drug metabolism and liver toxicity studies.
1.0 Empty Chamber Referring to FIG. 1, the chamber (10) is generally cylindrical in shape having a diameter (d), height (h) and a capacity or volume (v) appropriate to its function of liver perfusion. Typically this volume will be from 1-10 liters, more preferably 1-5 liters.

It is made of a material which can be sterilized (e.g. by autoclaving at 121° C. at 1 bar), will withstand cryopreservation temperatures (−160° C.) and can also withstand the rapid temperature change associated with these procedures. Additionally, the material should be compatible with the presence of those biological materials and solutions which it will contain, e.g. blood, plasma, saline, cryopreservatives, culture media etc.

It is a sealable unit comprising a walled cylindrical housing (36) enclosed by upper and lower plates (12, 14). As, in at least one mode of operation, it functions as a fluidised bed it comprises a fluidising inlet (16) in lower plate (14) and a fluidising outlet (18) in upper plate (12). These inlets/outlets can be used to introduce solutions including: culture media, plasma and cryoprotectants. A fluid bed support (20) comprising a plurality of orderly positioned holes (22), which assist in controlling fluidisation, is held in place by an O-ring (24) at the lowermost end of the chamber. Disposed over the fluid bed support is a mesh filter (26) which is held down by a wire ring (28). The filter serves to entrap alginate beads (120—FIG. 2) within the chamber during all stages of fluidisation and usage.

The chamber further comprises a fluid transport system (30) which enters the chamber at inlet (32) just above the fluid bed support (20) and exits the chamber at outlet (34) towards the upper plate (12). The fluid transport system takes the form of a tube which is preferably arranged helically, and in a regular pattern, around the inner wall (36) of the cylinder although other configurations are possible. The tube, which is semi-permeable to gases, will facilitate gas exchange (its primary function) to the fluidised biological component (100) (not shown for clarity). It can be made from silicone or any other suitable material, e.g. polymers which are gas permeable, non toxic, and can withstand the temperatures that will be experienced in operation. The material should also exhibit a degree of flex such that the tube can absorb the expansion which occurs when the contents of the chamber are frozen. The fluid transport system may additionally act as a heat exchange as fluids (liquids or gasses) are pumped there through.

Finally, the chamber comprises one or a plurality of heat exchange elements (38) which in one embodiment extend down through upper plate (12) into the chamber to just above the fluid bed support (20). These elements are arranged to be substantially perpendicular to the plates (12, 14) and are arranged in a regular pattern (being substantially evenly distributed) within at least a part of the volume of the chamber so as to maximise even and efficient freezing and thawing whilst minimising their effect on fluidisation. To this end, in a preferred embodiment, the heat exchange elements (which in one embodiment comprise hollow rods made from or coated with titanium and alloys thereof to maximise heat exchange) are disposed along one length (h) of the chamber, such that when the chamber is placed horizontally (FIG. 3b) (in contrast to its vertical fluidising, position (FIG. 3a)) it is able to efficiently cool/warm the biological component which is distributed favourably from a mass transfer perspective. It is important that the materials are non-toxic to the biological component and are not corroded by e.g. saline.

In an alternative arrangement the one or a plurality of heat exchange elements (38) may pass directly through the upper and lower plate in a straight path. Such an arrangement may simplify the pumping or pulling of a coolant fluid through the tubes. Indeed, in such an embodiment the tubes may have funnel shaped ends.

As, has been hinted at above with reference to the heat exchange elements (38) and fluid transport system (30), "scale up" brings with it issues of ensuring supply of e.g. oxygen and nutrients to the cells and exchange of e.g. proteins from the cells to e.g. blood/plasma. Accordingly, to assist in the exchange it is preferred that the cylinder has an aspect ratio (a), a=h/d, of from 10:1 to 1.3:1 and a capacity (v) of between 1 and 10 liters.

Whilst aimed at human liver cell lines in this instance, this design is generic for proliferating mammalian epithelial cells and would be applicable to other biomass requirements. For more details on the favoured biological component see section 2.0.

Figure 2A:
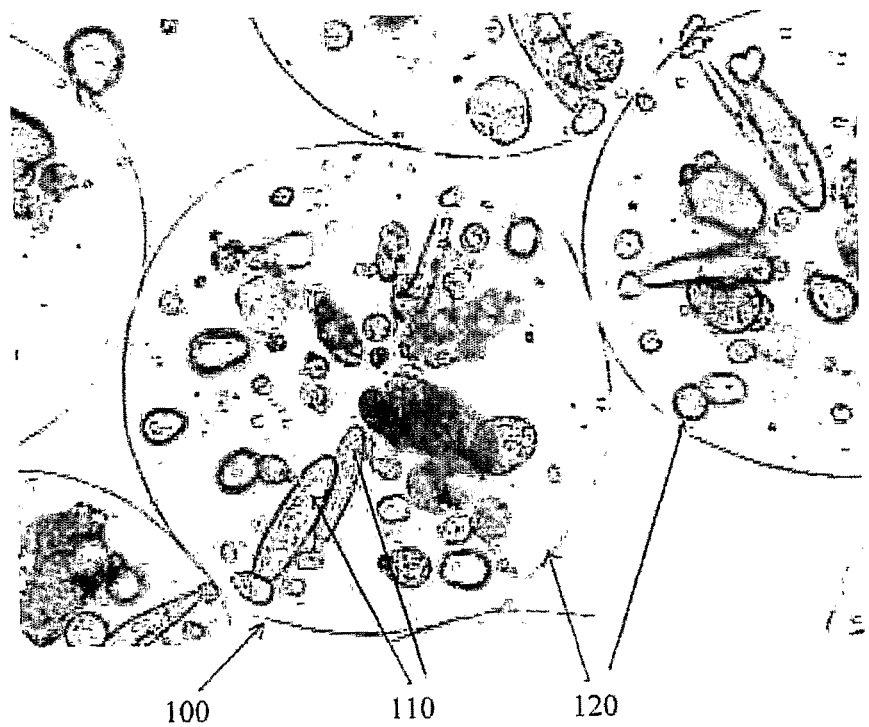
FIGS. 2A and 2B are phase contrast images of the biological component.
Figure 2B:
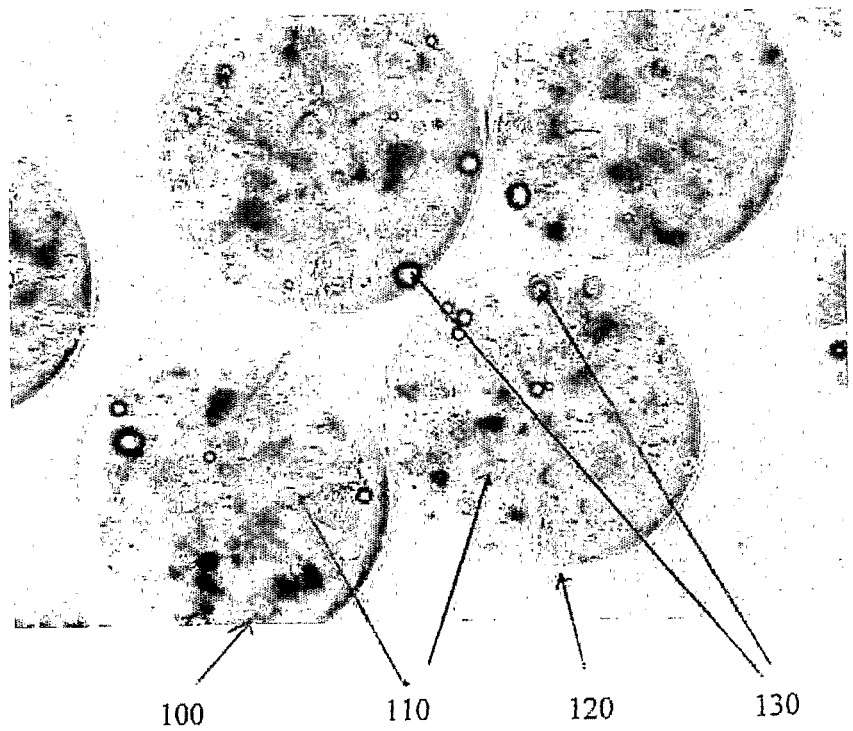

Oxygenation can be provided in a number of ways including simple gas exchange through gas permeable membranes, hollow fibre oxygenators and/or utilising perfluorocarbon mixtures with high oxygen saturation capabilities 2.0 Biological Component Referring to FIGS. 2A and 2B, the biological component (100) comprises a plurality of cells (110) encapsulated in alginate beads (120) of approximately 400 μm in diameter. The alginate beads also comprise a plurality of density modifiers (130) in the form of glass beads.

The individual cells are encapsulated to achieve approximately 18 to 25 million cells per milliliter of beads at performance competence. This 3-D alginate encapsulation system can of course be used for any proliferating epithelial cell lines so should functionally better cell lines emerge the technology will be equally effective. Development of alternative proliferating human cell lines, exhibiting a hepatocyte phenotype include differentiated hepatocyte cell lines from human embryonal, or cord blood stem cells.

3.0 Bio-Artificial Liver (BAL) Device

Figure 3A:
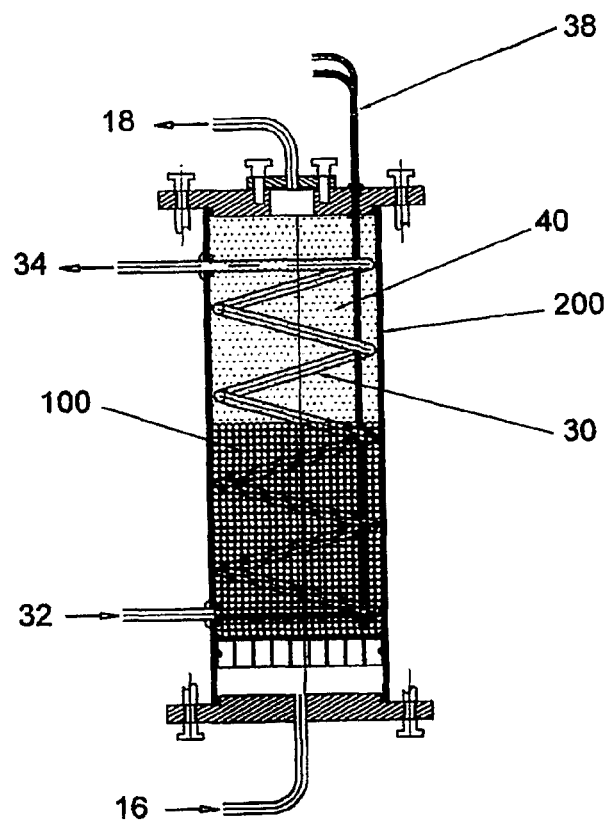
FIG. 3A is a cross sectional view of a BAL in the vertical (general use) position.
Figure 3B:
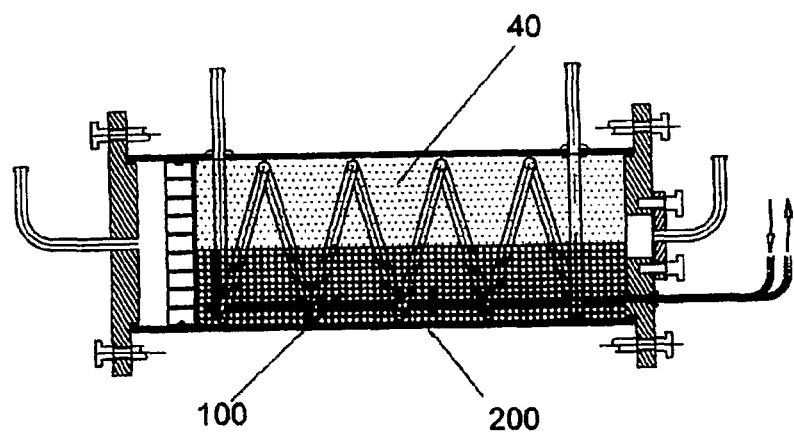
FIG. 3B is a cross sectional view of a BAL in the horizontal (cryopreservation) position.

The BAL device is illustrated in more detail in FIGS. 3A, and 3B. When the chamber (10) is filled with the biological component (100) it becomes, or at least has the potential to become, a bio-artificial liver (200) which may be used in an extracorporeal perfusion circuit (50).

To function as a bioartificial liver (200), the chamber (10) should comprise a volume (v) which is filled with sufficient biological component (100) and an appropriate solution (40), e.g. plasma, to function substantially, but temporarily, as a liver. (I.e. be fit for purpose). To this end, because the chamber functions as a fluidised bed, the biological component will be fluidised and thus the chamber capacity should be from about 1.2 to 2 times the volume of the bead volume added.

Obviously the bead volume will depend on the functionality of the liver cells encapsulated within the beads. A human liver can function at about 15%, and the BAL has been modelled to provide a 30% function (twice the minimal requirement).

Thus, it should comprise performance competent cell spheroids in 1-2% alginate beads, of a density that will allow fluidisation in human plasma. Performance competent cell spheroids will have been cultured for from 8-12 days and will contain anywhere from 18-60 million cells per ml of beads.

In order to achieve this, a yield of ~1 billion cells ($1 \times 10^9$) will be used to seed each 500-666 ml of alginate beads, and multiples thereof, such that the chamber will contain between $3 \times 10^{10}$ to $1 \times 10^{11}$ performance competent cells.

The alginate beads (120) will have a mean diameter of between 300-1200 μm, preferably 400 μm, and will additionally contain glass beads (130) with a mean diameter of between 10-50 μm in sufficient number to control the density for fluidisation to up to two times bed volume. The biological component (100) will be provided in an appropriate solution (40), either culture medium (during proliferation), isotonic fluid (pre use), plasma (pre- and during perfusion) or cryoprotectant (after proliferation when stored) depending on the phase of use.

In use the chamber will initially be fluidised at flow rates of between 50 ml/min and 1200 ml/min to achieve a 1.2 to 2-fold bed expansion.

However, moving from the use of cell lines on a lab scale (70 ml or less) to the development of a bio-artificial liver brings with it new challenges including the need to develop scalable methods and an understanding of how biological materials will function in the volumes necessary for use in liver perfusion on human subjects. It requires the multi-disciplinary expertise of mechanical engineering, mathematical modelling, biochemical engineering, materials science, theoretical physics, as well as medical expertise.

Significantly, the Applicant has now been able to demonstrate, on scales of up to 200 ml, that this Fluidised bed chamber design of a BAL device, utilising 3-d spheroids of human liver-derived cell lines, can achieve metabolic performance akin to that found in vivo and in primary hepatocytes.

For example, sampling the reservoir of culture medium by collecting 1 ml samples and analysing them has demonstrated:

glucose consumption of 4.98 μmoles glucose/million cells/day;
similarly protein synthesis (to a human liver);
secretion of albumin which demonstrate values in the same order of magnitude as that found in vivo, i.e. 12 g/$10^{12}$ liver cells/day; and (utilising oxygen probes measuring dissolved oxygen)
oxygen consumption of approximately 19 μmoles O/min/mg protein.

Manifestly, any artificial liver must be capable of being manufactured and distributed efficiently and safely, using processes that comply with GMP requirements.

Applicant has additionally developed a means of storing the performance competent beads for up to 3 days at room temperature and pressure at a high bead to medium ratio by using oxygen saturated perfluorodecalin (an oxygen carrier with much higher saturation than aqueous solution).

This is important as it would allow a manufacturer to "defrost" a device containing performance competent cells and ship it direct to a user (who wouldn't need to defrost the device at the point of use) making it simpler to use and less prone to user error.

Some of the challenges faced, and the independent solutions identified are set out in sections 5.0 to 7.0, but first the use of the BAL is described:

4.0 Modification for in-Line Patient Use

The final treatment phase will comprise connecting the bio-artificial liver device (200) (chamber (10) containing proliferated cells (100)) into a circuit (50) such that it is perfused with human plasma (40).

Thus, in use the BAL (200) will be connected to a patient such that plasma (40) enters the chamber (10) at, for example, inlet (16) and exits at, for example, outlet (18).

Figure 4:
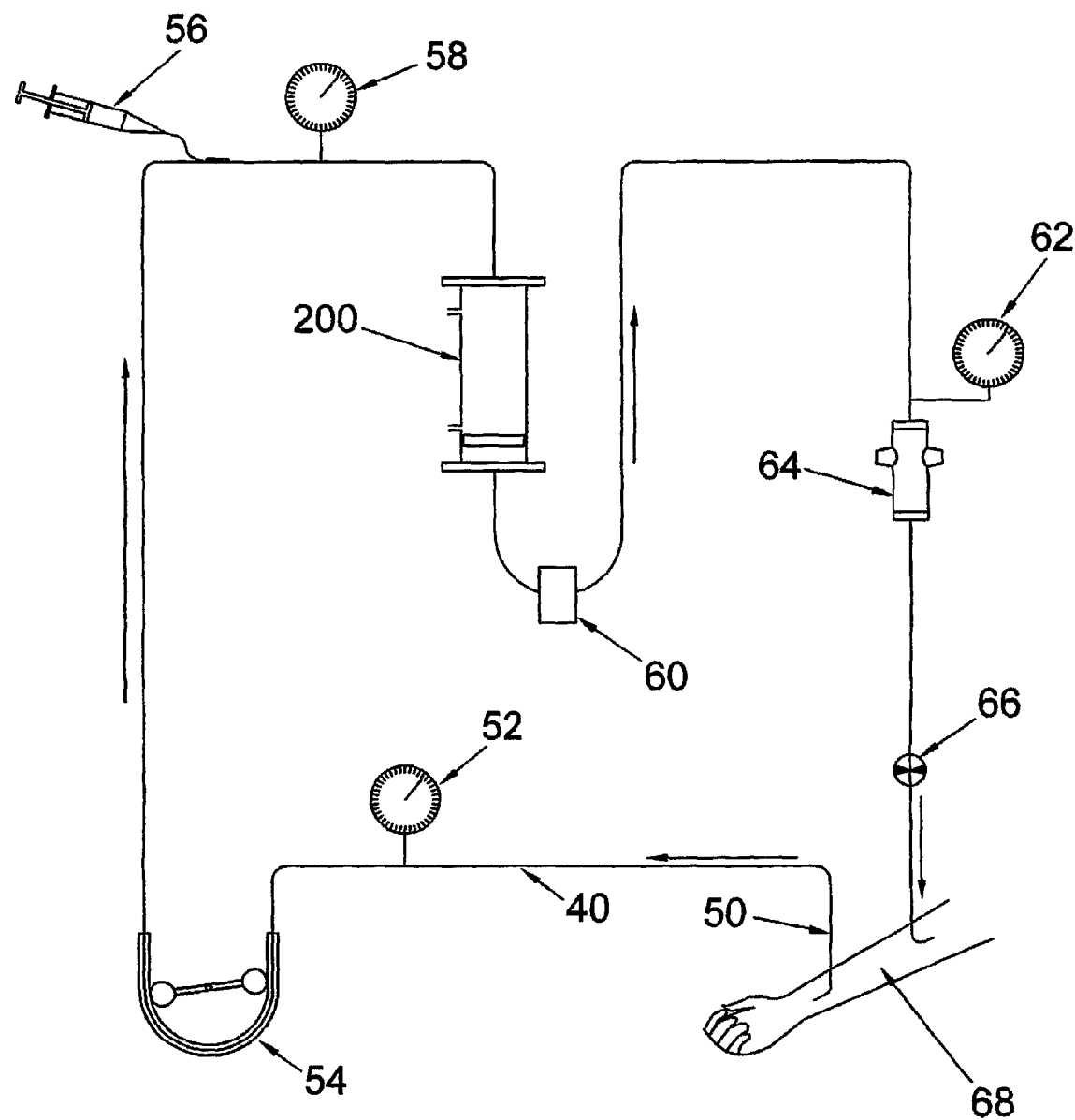
FIG. 4 shows a BAL in a circuit for in line use.

Referring to FIG. 4, either whole blood is perfused in a circuit (50) or blood is removed from a patient (68) and the plasma (40) is separated from the blood cells and passes through a circuit (50), and through the BAL (200) before being reintroduced to the blood cells and returned to the patient. Typically, but not essentially, the blood will pass through an arterial pressure monitor (52), the plasma separated, and be driven by a pump (54) to the BAL (200) via a heparin pump (56) and a perfusion inflow pressure monitor (58). In the BAL, the plasma is treated allowing exchange of e.g. toxins from the plasma to the cells (110) and proteins from the cells to the plasma. On leaving the BAL, the plasma passes through a DNA removal cartridge (60), is reintroduced to the blood cells through a venous pressure monitor (62), air trap (64), and air detector (66) before being returned to the patient.

Preferably the DNA removal cartridge comprises microporous hollow fibres with 1 μm pores to achieve a molecular weight cut-off of 2 million Daltons.

The cartridge should also contain a DNA binding cassette comprised of immobilised Deoxyribonuclease I enzyme to cleave DNA into di- and trinucleotides.

In use the device is fluidised to up to a two-fold bed height in the presence of human plasma as part of the extracorporeal circuit (50) that will enable the chamber to function as a clinically useful biomass.

A normal liver contains ~1-2×$10^{11}$ hepatocytes and ~15% of normal liver mass is required to sustain life in otherwise well individuals (1.5-3.0×$10^{10}$).

Accordingly, the applicant's system has been developed with the aim of providing 30% of a normal liver cell mass. This cell mass must be contained in a practical perfusion system with diffusion parameters that allow e.g. adequate access of oxygen and nutrients during the initial proliferation phase, and which allows transfer of toxins in, and metabolites, detoxified products and proteins out of cells for return to a patient during inline use in extracorporeal perfusion. In this regard the Applicant's system, benefits from the use of uncoated alginate gel beads which minimise diffusion barriers. It also comprises a geometry suitable for use in a human extracorporeal circulation, by allowing adequate numbers of cells to be contained in a volume which can be feasibly perfused in a device for human use. If required, more than one chamber can be used in parallel.

Blood flow through the portal vein is 1200 ml/min in man, and therefore, ideally the plasma should circulate through the chamber at a flow rate commensurate with in vivo conditions for the treatment regime. Previous work has indicated a flow rate of 400 ml/min may be adequate for this step so flow rates ranging from 50-1200 ml/min may be used.

5.0 Manufacture of the Biological Component 5.1 Lab Scale

At lab scale the applicant employed a technique using vibration to cause droplet formation of the alginate-cell suspension. Theoretically a multi-nozzle machine based on the same principle might have been used to achieve the necessary scale-up, but such a method would also amplify the inherent problems of this technology including nozzle blockage and an unstable stream.

To overcome these problems, the applicant has developed a scalable methodology as described below:

5.2 Large Scale

The applicant has carried out preliminary tests using a new technology (a rotating disc technology) with encouraging results. They have been able to produce beads (under sterile conditions) of an appropriate size 300-5000 μm and the pressure (2-25 psi) required, has surprisingly not proved detrimental to cell viability.

In order to optimise a custom built Jet cutter droplet maker for the scale required for clinical use (estimate based on 30% liver function—1.5-5 L of alginate beads) the following conditions were determined to be preferred:

Stirring rate—50-200 rpm,
Pressure/stream delivery—2-15 psi;
Flow rate—15-30 ml/min;

Cutting speed—3000-4000 rpm using 60-100 wire discs; and

Nozzle size—350 μm (range 250 μm—450 μm) and shape circular.

The alginate was seeded with 0.5-3 million/cells per ml of alginate-medium and densified with glass particles of 10-50 μm diameter in an amount of 1-5% w/v that will achieve continued suspension when perfused in human plasma.

The beads were polymerised for 10-60 minutes in calcium chloride solution containing one or more surfactants such as Pluronic acid or other pharmaceutically approved equivalents.

In addition, a method was established to maintain a calcium chloride concentration of 0.17M over the whole production period to ensure appropriate alginate polymerisation, without compromising cell viability. The applicant has found that when encapsulating large volumes of alginate, dilution of the calcium ions occurs, leading to a drop in the quality of beads produced over time. To overcome this problem, a concentrated solution of calcium chloride (70% w/v Ca Cb in 0.15M NaCl) is used to supply extra calcium ions to maintain the concentration during encapsulation. Additionally, an overflow on the bath ensures the total volume of calcium solution and beads in the bath remains constant.

Culture medium was used to equilibrate the beads prior to introduction into the multifunctional bioreactor chamber.

Further details of the methodology are set out below:

5.2.1 Encapsulation of HepG2 Cells in Alginate Using a GeniaLab JetCutter System The JetCutter unit was placed in a Class 2 hood. It comprised a pressure vessel which houses the material to be encapsulated, which material is forced under pressure through a nozzle into the path of a cutting tool, driven by a motor, where it is cut and the resulting material is directed into a collection bath where the material is polymerised.

The material may be made up as follows:
1) Into a 1-5 L glass or polypropylene beaker, with magnetic follower, HepG2 or other appropriate cells, are added to a 1:1 mixture of α-MEM culture medium and 2% alginate at the required seeding density (0.5-3.0×10$^6$ cells/ml);
2) 2-5% w/v of 10-50 μm glass beads are added, and the mixture is stirred to homogeneity using the magnetic follower;
3) A fill cap, on the lid of the pressure vessel, is removed and the mixture for encapsulation is added using a funnel;
4) The cap is replaced immediately, and a stirrer motor started at a speed appropriate for maintaining an even suspension of cells, glass beads and alginate-culture medium; typically speeds of 50-200 rpm may be used;
5) A compressed air line is used to apply pressure (start at around 0.25 bar). The tap on the pressure vessel outlet is opened to start the flow through the encapsulator;
6) The resulting stream is collected in a 25 ml measuring cylinder over 45 sec to measure the flow rate.
7) The inlet air pressure is adjusted until the flow rate=0.33-0.35 ml/sec;
8) The jet cutter is set to cut the stream. Typical run parameters, will include: flow rate=0.33 ml/sec, nozzle size=350 um, number of wires=60, wire diameter=100 μm, motor speed=3600 rpm;
9) The JetCutter software will calculate the optimal angle of inclination (typically 16 to 22 degrees, more particularly 18 to 20 degrees), which can then be manually set on the JetCutter itself;
10) The collection vessel for the beads may be a bowl with an overflow tube attached to the side of the bowl, and a 200 μm mesh filter. This overflow tube should be placed into a bottle to collect the waste calcium chloride solution from the bath, ensuring that the waste collection bottle is located below the collection vessel to allow the flow of liquid by gravity. The feed and bleed tubing outlet is attached to the side of the basin so that it overhangs the rim by approx 2 cm. This allows the concentrated calcium chloride solution to drip into the edge of the bath. The feed and bleed tubing is then connected to channel one of the for example, Watson Marlow 520DU/N pump with a C305A multi channel pump head attached. Finally, the inlet is placed in a bottle containing concentrated calcium chloride solution in 0.15M NaCl (recommended CaCb concentration 70%). The pump speed is set according to the Jetcutter flow rate used.
11) Collect the beads in the polymerisation buffer.

5.2.2 Collecting and Washing the Finished Beads
1) Transfer filter into a 1-5 L sterile vessel,
2) Rinse the beads, which remain on the mesh surface, with DMEM (3 times 500 ml medium for 5 minutes each per 400 ml beads) before adding DMEM until the beads are just covered;
3) Use a weighing spoon to scoop the beads into a sterile graduated vessel, re-suspend in α-MEM culture medium and allow to the beads to settle;
4) Repeat this process until all of the beads from the basin have been processed;
5) Once the beads have settled out estimate the volume of beads collected from the graduations on the side of the container 6.0 Cell Proliferation Methodology (Scale Up to 250 ml)

6.1 Lab Scale

The applicant has previously demonstrated the value of a "micro-gravity rotating cell culture system" as advantageous for the proliferation stage.

They have now determined that a fluidised bed bioreactor, in which alginate cells are maintained in continuous "suspension" in fluid, can also be used to achieve the same performance competent biomass. Such a process is scalable, and has advantages over the previously described lab scale method.

6.2 Large Scale

The Applicant has demonstrated a scalable method with 400 ml beads, which is compatible with the "modular" system of the invention. This is further described below:

6.2.1 Initial Proliferation Steps to Performance Competence
1. The device (200) is filled with culture medium (40) to the level of the filter (26) using a peristaltic pump to deliver medium thereto;
2. Encapsulated cells (100) are introduced to the chamber (10) via a fill port (not shown) in upper plate (12);
3. The remaining volume (v) of the chamber is completely filled with culture medium (40);
4. The BAL (200) is connected in the separate circuit (not shown) that supplies medium (40) via a peristaltic pump from the reservoir of a, for example, Celligen Plus bioreactor (New Brunswick Scientific) and returns it to the same reservoir via an inline dissolved oxygen probe;
5. The flow rate used is such that a 1.2 to 2 fold expansion of the packed bed of alginate beads (100) is achieved;
6. An automated bioreactor controller both monitors and controls the temperature, stirring rate, pH, and dissolved oxygen of the culture medium reservoir. This allows set points to be chosen which ensure that medium delivered to the fluidised bed bioreactor is optimal for encapsulated cell growth;
7. Approximately 50% of the volume of culture medium in the circuit is replaced after the first 48-72 hours of culture depending on cell density and from then on every 24 to 48 hours. A feed and bleed system is also available for more subtle control.

8. A cassette of immobilised enzymes in direct contact with the flow path will be introduced immediately prior to medium in contact with beads that recycle lactate to provide pyruvate (an energy source) and oxygen to the beads. The enzymes to be used will include, but not be limited to, lactate oxidase and catalase.

During proliferation, cytochrome P450 activity, may be enhanced by culturing with an inducer, such as, for example dibenzanthracene (at e.g. 6 um) for a time period of e.g. 24-72 hours. This can significantly elevate Cytochrome P450 levels for a period of days following induction (which remains sustainable once the inducer is removed) and can furthermore, on subsequent exposure result in further elevation.

Alginate encapsulated cells (100) can be removed from the chamber (10) during proliferation and are typically maintained for 8 to 12 days in order for encapsulated cells to reach performance competence.

7.0 Cryopreservation
7.1 Lab Scale

The applicant has shown on a small scale that alginate encapsulated liver cell lines are cryopreservable, and recover function rapidly on thawing and maintain stable function over an appropriate time span for use. (Khalil M, Shariat-Panahi A, Tootle R, Ryder T, McCloskey P, Roberts E, Hodgson H, Selden C. Human hepatocyte cell lines proliferating as cohesive spheroid colonies in alginate markedly upregulate both synthetic and detoxificatory liver function. Journal of Hepatology 2001; 34: 68-77.)

7.2 Large Scale

Heat transfer during Cryopreservation will be achieved using liquid nitrogen vapour either by via controlled rate freezing or by vitrification. Thawing will be achieved similarly with sterile warm gas and in addition warm fluid pumped through the vessel.

Cryopreservation to −160° C.

As cryoprotectant addition to cells is an exothermic process the mass needs to be pre-cooled prior to the cryoprotectant being added; however, once cryoprotectant has exchanged with the aqueous components the whole system must be rapidly cooled either at a controlled rate of ~1-4° C./min, or by plunging into liquid nitrogen to −190° C.; after a period of equilibration it should be transferred to vapour phase of liquid nitrogen at −160 C.

The beads containing functional spheroids will be cooled to 0° C., exposed to cryoprotectants, further cooled using a combination of cooled liquid, and liquid nitrogen to achieve controlled rate freezing to ~−160° C. where they will be stored until required. The former step will be conducted in the vertical position, the later step in the horizontal position.

Pre-cooled cryoprotectant will be exchanged (in the vertical position FIG. 3A) with the aqueous components of the whole system prior to rapid cooling at a controlled rate (~1-4°/min) to −160 C. After a period of equilibration it will be transferred to vapour phase of liquid nitrogen for rapid freezing. This is done with the chamber in the horizontal position (FIG. 3B). This will allow distribution of beads (100) along the length (h) of the chamber, thereby reducing the path length across which the temperature drop occurs. Liquid nitrogen cooling will be distributed through titanium/alloy tubes (38) disposed to one side of the chamber.

Rapid thawing and restoration of 37° C. and recovery of full function Warm air followed by warm liquid (+/−microwave heating) will raise the temperature to −7° C. initially, then to 1° C. when cryoprotectants will be removed by replacement of bead milieu with culture medium. Thereafter slow heating to 37° $C._1$ followed by perfusion with nutrient and oxygen rich media will restore full activity over 24-48 hours.

The thawing procedure must bring the beads back to 37° C. without ice crystal formation and allow rapid removal of cryoprotectant at <4° C., and replacement with initially fresh culture medium at 4° C., prior to subsequent addition of fresh medium at 37° C. warming the chamber to 37° C. rapidly.

As well as removal of the cryoprotectant there will be need for rapid re-oxygenation; use of gas permeable tubing (30) to achieve this will be used. (The same tubes may allow for expansion of liquids as they freeze.) In addition a oxygen saturated perfluorocarbon solution will be dispersed throughout the chamber.

8.0 Summary of a Functionally Modular Approach

There are a number of distinct steps involved in arriving at a final product; that being a chamber of cells to which the patient's circulation can be attached, and the provision of such a chamber at the bedside of the sick patient. Those steps are:

The preparation of the cells ($10^{10}$ to $5 \times 10^{10}$ for one complete BAL which may contain more than one chamber) by large scale monolayer culture;

Harvesting of cells from monolayer culture into suspension;

Mixing cells with alginate;

"Encapsulation of individual cells" (approximately 60-100 per bead) into alginate droplets (approximately 100-200 million per chamber);

Maintenance of alginate droplets in culture, for eight to twelve days during which time the liver cells proliferate as coherent spheroids to provide a performance competent biomass;

Cryopreservation of Spheroids biomass: Performance competent cells in beads must be available for use in a patient within 48 hours of hospitalization. The biomass must therefore be cryopreserved and stored at −160 C until required;

Thawing of Spheroids biomass: the biomass must be rapidly thawed and regenerated to full performance within 24-48 h of a request.

The sequential, and integrated approach described can give rise to a device and methodology that can benefit patients.

The invention claimed is:

1. A chamber for the biological component of a bio-artificial liver comprising a fluid bed support, at least one heat exchanger element disposed in the chamber, a fluidising inlet and a fluidising outlet and is configured to allow:

Proliferation of the biological component, in situ via the fluidising inlet and the fluidising outlet when the chamber is in a vertical position;

Cryopreservation of the biological component, in situ via the at least one heat exchanger element when the chamber is in a horizontal position; and Perfusion of the biological component, in situ via the fluidising inlet and the fluidising outlet, in an extracorporeal circuit attached to a patient, when the chamber is in the vertical position;

wherein the at least one heat exchanger element is arranged off-centered in the chamber when in the vertical position, such that when the chamber is in the horizontal position, the biological component is spread such that a larger surface area of the biological component comes into contact with an outer wall of the chamber and the at least one heat exchanger element than when the chamber is in the vertical position.

2. A chamber as claimed in claim 1 which can be sterilised.

3. A chamber as claimed in claim 1 which is a sealable unit of tubular construction comprising a wall closable by upper and lower plates.

4. A chamber as claimed in claim 1 comprising a working volume of from 1 to 10 liters.

5. A chamber as claimed in claim 1 which is substantially cylindrical, and has an aspect ratio, a=h/d, where h=height and d=diameter, of from 10:1 to 1.3:1.

6. A chamber as claimed in claim 5 further comprising a filter mesh.

7. A chamber as claimed in claim 1 further comprising an inlet and outlet and a fluid transporter system disposed there between.

8. A chamber as claimed in claim 7 wherein the fluid transporter system comprises a tube semi-permeable to gasses.

9. A chamber as claimed in claim 7 wherein the fluid transporter system is arranged helically around inner wall.

10. A chamber as claimed in claim 1 wherein the wherein the at least one heat exchanger element extends through an upper plate into the chamber above the fluid bed plate.

11. A chamber as claimed in claim 10 wherein the at least one heat exchanger element is arranged substantially perpendicular to the upper and lower plates.

12. A chamber as claimed in claim 1 wherein the at least one heat exchanger element is disposed along one length of the chamber.

13. A chamber as claimed in claim 1 wherein the at least one heat exchanger element is a hollow rod made or coated with titanium or alloys thereof.

14. A chamber for a biological component of a bio-artificial liver comprising:
   a fluid bed support;
   a fluidising inlet;
   a fluidising outlet; and
   at least one heat exchanger element disposed in the chamber;
   wherein the biological component is disposed in the chamber;
   wherein the fluidising inlet and the fluidising outlet proliferate the biological component in situ within the chamber when the chamber is in a vertical position;
   wherein the at least one heat exchanger element cryopreserves the biological component in situ within the chamber when the chamber is in a horizontal position;
   wherein the fluidising inlet and the fluidising outlet perfuse the biological component in situ within the chamber when part of an extracorporeal circuit attached to a patient when the chamber is in the vertical position; and
   wherein the at least one heat exchanger element is arranged off-centered in the chamber when in the vertical position, such that when the chamber is in the horizontal position, the biological component is spread such that a larger surface area of the biological component comes into contact with an outer wall of the chamber and the at least one heat exchanger element than when the chamber is in the vertical position.

15. A chamber as claimed in claim 14 further comprising a fluid transporter system disposed in the chamber.

16. A chamber for a biological component of a bio-artificial liver comprising:
   a fluid bed support;
   a fluidising inlet;
   a fluidising outlet;
   at least one heat exchanger element disposed in the chamber; and
   wherein the biological component is disposed in the chamber and comprises a matrix forming agent comprising a plurality of cells and one or more density modifiers, wherein the cells are a proliferating human cell line exhibiting a hepatocyte phenotype;
   wherein the chamber further comprises at least one of an isotonic solution and a cryopreservant;
   wherein the fluidising inlet and the fluidising outlet proliferate the biological component in situ within the chamber when the chamber is in a vertical position;
   wherein the at least one heat exchanger element cryopreserves the biological component in situ within the chamber when the chamber is in a horizontal position;
   wherein the fluidising inlet and the fluidising outlet perfuse the biological component in situ within the chamber when the chamber is in the vertical position; and
   wherein the at least one heat exchanger element is arranged off-centered in the chamber when in the vertical position, such that when the chamber is in a horizontal position, the biological component is spread such that a larger surface area of the biological component comes into contact with an outer wall of the chamber and the at least one heat exchanger element than when the chamber is in the vertical position.

* * * * *